United States Patent [19]

Taylor et al.

[11] E Patent Number: Re. 33,307

[45] Reissued Date of Patent: Aug. 21, 1990

[54] CYCLIC HYDROXY COMPOUNDS

[75] Inventors: Stephen C. Taylor, Darlington; Michael D. Turnbull, Earley, both of England

[73] Assignee: Imperial Chemical Industries PLC, London, England

[21] Appl. No.: 292,348

[22] Filed: Dec. 30, 1988

Related U.S. Patent Documents

Reissue of:

[64] Patent No.: 4,740,638
Issued: Apr. 26, 1988
Appl. No.: 59,813
Filed: Jun. 9, 1987

[30] Foreign Application Priority Data

Jun. 19, 1986 [GB] United Kingdom ..... 8614925

[51] Int. Cl.[5] ..... C07C 35/14; C07C 43/196; C07C 43/253

[52] U.S. Cl. ..... 568/832; 568/608; 568/622; 568/623; 568/631; 568/635; 568/833

[58] Field of Search ..... 568/832, 608, 622, 631, 568/635, 833, 841, 842, 812, 822, 823, 815

[56] References Cited

FOREIGN PATENT DOCUMENTS

| | | | |
|---|---|---|---|
| 468280 | 10/1944 | Canada | 568/833 |
| 520343 | 12/1976 | U.S.S.R. | 568/834 |
| 773402 | 4/1957 | United Kingdom | 568/833 |
| 1043507 | 9/1966 | United Kingdom | 568/822 |

OTHER PUBLICATIONS

Gogek et al., "Canadian J. Chem.", vol. (1951), pp. 938–945.

Shepard et al., "Industrial & Engineering Chem.", vol. 20 (1929, pp. 722–723).

Wackett, "Aromatic Hydrocarbon Metabolism and Bacterial Enzymes", University of Texas at Austin, University Microfilms International (1984).

*Primary Examiner*—Werren B. Lone

*Attorney, Agent, or Firm*—Cushman, Darby & Cushman

[57] ABSTRACT

Novel substituted cis-1,2-dihydroxy-cyclohexa-3,5-diene compounds, useful as intermediates in the production of phenols and catechols for use as intermediates in the production of drugs, herbicides, insecticides and as chiral synthons, in particular cis-1,2-dihydroxy-3-trifluoromethyl-cyclohexa-3,5-diene. A process for producing the novel compounds is also claimed.

10 Claims, No Drawings

CYCLIC HYDROXY COMPOUNDS

Matter enclosed in heavy brackets [ ] appears in the original patent but forms no part of this reissue specification; matter printed in italics indicates the additions made by reissue.

This invention relates to novel cyclic dihydroxy compounds and to a process for producing them.

Certain cis1,2-dihydroxycyclohexadienes are useful in the preparation of novel polymers. In our European Patent Specification No. 76606 B we disclose a process for the production of such dihydroxy cyclohexadienes from aromatic compounds using mutant strains of the species Pseudomonas putida, in particular mutants of P. putida strains NCIB 11767 and NCIB 11680. The enzyme which catalyses the reaction involved in this process in an aromatic dioxygenase which catalyses a reaction between certain aromatic compounds and oxygen for example the reaction below between benzene and oxygen

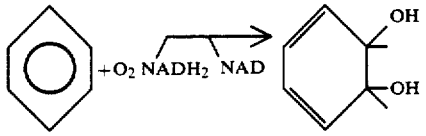

When strains such as P. putida NCIB 11767 and NCIB 11680 are fed with aromatics, the dihydroxy cyclohexadiene compounds do not accumulate since they are rapidly further oxidised via catechols to products of intermediary metabolism. However in our European Specification No. 76606 we describe how mutants of these microorganisms may be produced which are unable to oxidise the dihydroxy cyclohexadienes and these compounds as a result accumulate when such mutants are exposed to aromatic substrates. Some of these mutants must be grown in the presence of benzene or toluene if the activity of the aromatic dioxygenase enxyme needed to convert aromatics to dihydroxy cyclohexadienes is to be induced. Some of the mutants are constitutive for the enzyme which causes production of the dihydroxy cyclohexadienes ("constitutive strains"). These constitutive strains do not require prior enzyme induction by benzene or toluene in order to produce dihydroxy cyclohexadienes.

In the parent of the present divisional application we disclose an improved method for the production of cells of Pseudomonas putida comprising an enzyme capable of converting an aromatic or substituted aromatic compound to a corresponding cyclic dihydroxy compound comprising a 1,2-dihydroxy-cyclohexa-3,5-diene ring which comprises growing cells of a first mutant strain of Pseudomonas putida (as hereinafter defined) in a culture medium containing an inducer compound other than benzene or toluene which causes induction of the enzyme capable of converting the aromatic or substituted aromatic compound to the corresponding cyclic hydroxy compound and which is not itself a substrate for said enzyme.

Alternative processes for the production of cyclic dihydroxy compounds from aromatics which are described in the literature include that described by Gibson D. T. et al, Biochemistry, 9, 1970, 1626–1630.

The process of our European Pat. No. 76606 B, particularly when carried out using microbial cells produced by the method of the parent of the present application enables conversions of aromatic compounds to be achieved to produce some interesting new cyclic dihydroxy compounds.

According to the present invention we provide compounds having the general formula:

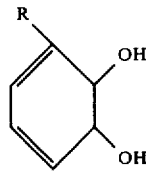

wherein

R is —C trihalide, —O alkyl or —O phenyl group.

A preferred compound according to the invention is that in which R is $—CF_3$.

Further according to the present invention we provide a process for the production of a cyclic dihydroxy compound having the general formula:

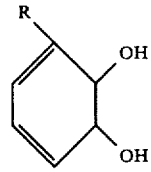

wherein R is a —C trihalide, —O alkyl or —O phenyl group, which comprises supplying a corresponding substituted aromatic compound, having the general formula:

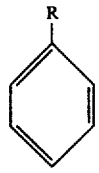

and an energy source to a strain which is a first mutant strain or a constitutive mutant strain of Pseudomonas putida (both as hereinafter defined) in a medium which supports little or no growth of cells of the strain.

When the preferred compound of the invention is to be produced by the process of the invention R in the substituted aromatic compound will be $—CF_3$.

The first mutant strain is a strain of Pseudomonas putida:

(a) in which an enzyme can be induced which can convert an aromatic or substituted aromatic compound into a corresponding cyclic dihydroxy compound, (b) which is not capable of growing on benzene or toluene, and (c) which is derived from a strain P. putida which is capable of growth on benzene or toluene.

The constitutive mutant is produced from the first mutant strain of P. putida and is constitutive for an enzyme which converts an aromatic or substituted aromatic compound into a corresponding cyclic dihydroxy compound.

Preferably the first mutant strain is derived from P. putida strain NCIB 11680 or NCIB 11767 deposited at the National Collection of Industrial Bacteria, Torrey Research Station, Aberdeen, Scotland, UK.

Examples of suitable energy sources for the process of the invention include, alcohols such as ethanol, carboxylic acids such as acetic acid and carbohydrates such as glucose. Preferred energy sources are ethanol and acetic acid.

Strains which are very suitable as first mutant strains in the method or the process of the invention, may be prepared by treating Pseudomonas putida NCIB 11680 or preferably Pseudomonas putida NCIB 11767 under mutating conditions therefore to give mutant strains which are no longer capable of utilising toluene or benzene as a sole source of carbon for growth and which when grown, in a liquid medium containing pyruvic acid as a carbon source, in the presence of toluene, excrete a substance which has a UV absorbance peak at 265 nm. This mutation may be effected by chemical and/or physical means. Chemical mutation may be effected for example by treatment of the microorganism with N-methyl-N'-nitrosoguanidine, e.g. as described by Ornston, Journal of Biological Chemistry, 1966, Volume 241, pages 3800–3810. Physical mutation may be effected by electromagnetic radiation, e.g. UV light.

The constitutive mutant strain for use in the process of the invention is suitably prepared by treating the first mutant strain of Pseudomonas putida NCIB 11767 under mutating conditions as hereinbefore described to give strains which after growth in the absence of an aromatic compound, have the ability to produce cyclic dihydroxy compounds from aromatic compounds. Choice of suitable constitutive strains from the product of the mutation treatment may be facilitated by growing the cells after mutation on a solid agar medium containing pyruvic acid or glucose as carbon source. After growth, the colonies on the agar plates may be sprayed with a solution of catechol in water, colonies of cells which rapidly turn yellow/green are constitutive for an enzyme which converts catechol into 2-hydroxymuconic semialdehyde (Nozaki, Topics in Current Chemistry (English Review) 1979, Volume 78, pages 145–186). This enzyme catalyses one of the steps in the oxidative degradation of benzene in Pseudomonas putida NCIB 11680 and Pseudomonas putida NCIB 11767 and we have found that it is linked in its expression to the enzyme which converts benzene to the cyclic dihydroxy compound. Therefore those cells which turn green on exposure to catechol are the desired constitutive strain.

The constitutive mutant strain may be susceptible to catabolite repression by carbon sources such as glucose and casamino acids. Improved constitutive strains which are not susceptible to such catabolite repression may be obtained by further mutation of the constitutive strains, by treatments as hereinbefore described. The improved constitutive strains can be detected by growing colonies of the constitutive strains which have been subjected to a mutation treatment on an agar medium which contains a mixture of glucose and casamino acids as carbon sources, the colonies which turn yellow/green on exposure to catechol comprise the improved constitutive strain.

When the first mutant is produced by the method of the parent of the present application, cells of the mutant strain may be grown in conventional growth media (modified to include an inducer compound) as a continuous, batch or fedbatch technique.

The growth medium in which first mutant strains for use in the process of the invention may be grown comprises an aqueous mineral salts solution and a suitable carbon source. The carbon source may be, for example, acetic acid, glucose or ethanol. The concentration of carbon source can vary over a wide range but is generally between 1% (w/w) and 20% (w/w). Oxygen or an oxygen containing gas, must be present during the growth period. The temperature of the medium during the growth period may vary considerably but normally will be in the range of 25° C. to 35° C. The pH of the medium is kept within the range of 5.5 to 8.0 during growth and preferably at 6.5 to 7.5. The size of the culture can vary considerably for example between 1.5 and 500 liters.

Following the growth period the cells are used in the process of the invention. The cells may be harvested, for example by centrifugation or flocculation, or they may be used directly in the process of the invention. Where the cells are harvested they are resuspended in a mineral salts solution which does not support significant cell growth, e.g. phosphate or buffer solutions or a growth medium which is conventional but lacks or contains little of one or more essential elements. Typically the concentration of resuspended cells is 1 to 30 grams dry weight per liter. The cells are kept at a temperature of 20° C. to 40° C. and the pH maintained between 6.5 and 8.5. Oxygen or an oxygen containing gas is added to the cell suspension such that the oxygen tension is kept at greater than 1% of saturation. A suitable energy source is supplied, to the cell suspension such that the concentration of the energy source is maintained at a suitable concentration, preferably between 0.05% (w/w) and 0.5% (w/w).

The substituted aromatic compound may be added to the cell suspension as a vapour in the stream of oxygen or oxygen-containing gas but preferably, when it is liquid, it is added as a liquid.

The rate of addition of the substituted aromatic compound to the culture of the mutant strain in the process of the invention is typically about 0.5 to 10 grams per gram dry weight of cells per hour. The rate of addition of the energy source may vary during the conversion but is typically in the range 0.1 to 2.0 grams per gram dry weight of cells per hour. The productive lifetime of the cell suspension is typically between 5 and 50 hours. After this period the cells are removed by centrifugation and/or flocculation. Fresh cells may be added to the supernatant liquor and the process repeated. At the end of the process the supernatant liquor typically contains between 10 and 50 grams per liter of a compound of the invention.

The new cyclic dihydroxy compounds produced by the process of the invention are preferably extracted from the aqueous reaction mixture by solvent extraction with a suitable polar solvent. Examples of polar solvents which may be used include inter alia ethyl acetate, diethyl ether and methylene chloride. More preferably continuous extraction procedures are employed. However, we do not exclude the possibility that, for example, the aqueous medium, after separation of the cells, is evaporated and the residue dissolved in a suitable solvent, e.g. methanol, ethanol or methylene chloride.

The dihydroxy compounds prepared by the process of the invention may be converted into derivatives thereof, e.g. acetate, benzoate, privalate, carbonate, which derivatives may be converted into polymers and copolymers thereof.

The new compounds of the invention can be used to produce phenols and catechols which are useful as intermediates in the production of drugs, herbicides and insecticides or as chiral synthons from which for example certain natural products may be synthesised.

Growth media used in preparation of mutants and in Examples

1. Bauschop and Elsdon's medium as described in Journal of General Microbiology, 1960, Volume 23, pages 457–469.
2. Luria liquid medium as described in "Experiments in Molecular Genetics" by J H Miller, published by Cold Spring Harbor Laboratories, New York, 1972.

Preparation of mutant strains of Pseudomonas putida NCIB 11767 for use in the present invention Pseudomonas putida NCIB 11767 was grown to early exponential phase in Luria liquid medium. The cells were harvested by centrifugation and resuspended at a concentration of 0.2 grams dry cell weight per liter in 20 ml of 25 millimolar citric acid-sodium citrate buffer, pH 5.5 containing 1 mg of N-methyl-N'-nitro-N-nitroso-guanidine (NTG). After 45 minutes at 30° C. the cells were harvested by centrifugation, washed twice with Bauschop and Elsdon's medium and then grown overnight in this medium when containing 0.3% (w/v) sodium pyruvate at 30° C. After serial dilution, cells were plated on a Bauschop and Elsdon's medium agar containing 0.3 millimolar sodium pyruvate and incubated in 1 liter paint tins each containing 0.5 ml benzene in a vial. After 3 days at 30° C. 144 prospective mutants, i.e. colonies less than 0.5 mm diameter, were picked off and regrown on a 0.2% w/v sodium pyruvate, Bauschop and Elsdon's medium agar.

90 of these mutants were screened in liquid culture for the production from benzene of a compound absorbing at 260 nm. One mutant which gave a supernatant liquid with a maximum absorbance at 260 nanometers of 37 is hereinafter referred to for convenience as mutant strain B.

Preparation of constitutive strains from Mutant B

The procedure used for mutagenisis was as hereinbefore described. After treatment with NTG, the washed, diluted cells were plated onto Bauschop and Elsdon's medium agar plug 10 millimolar sodium pyruvate. After two days at 30° C., colonies were sprayed with a solution of catechol in water (0.5 molar) and those which turned yellow/green after 5 minutes were selected. From a total of $1.8\times10^5$ colonies screened, 35 yellow/-green colonies were selected. Each of these was grown overnight in 16 ml of Bauschop and Elsdon's medium plus 0.3% (w/v) sodium pyruvate. Cells were harvested and resuspended in 10 ml of 25 mM potassium phosphate buffer, pH 7.8, containing 0.4% (v/v) ethanol. These cultures, in 20 ml conical flasks, were incubated overnight, each in the presence of 0.5 ml toluene. Supernatants were examined after this time of compounds absorbing at 265 nm. A constitutive mutant which gave an absorbance at 265 nm of 250 was selected and is hereinafter referred to for convenience as mutant strain C.

Mutant strain C was grown at 30° C. in 20 ml of Luria liquid medium to early exponential phase and after harvesting, cells were resuspended in 40 ml of 0.1 molar $MgSO_4.7H_2O$. A 5 ml aliquot was UV-irradiated in a glass petri dish for 45 seconds at a dose of 1.6 $uW/cm^2\times100$. The cells were then grown in the dark in five 20 ml aliquots of Bauschop and Elsdon's medium plus 10 millimolar sodium pyruvate.

After 2 days at 30° C. cultures were serially diluted and plated onto Bauschop and Elsdon's medium plus 75 millimolar glucose and 1% (w/v) vitamin free casamino acids (ex Difco Ind., Detroit, Mich., USA) and incubated for a further 2 days at 30° C. Colonies were then sprayed with catechol as hereinbefore described and yellow/green colonies were selected. From a total of $4\times10^4$ colonies screened, 10 were selected and grown overnight in 10 ml of Bauschop and Elsdon's medium plus 75 millimolar glucose and 1% (w/v) casamino acids at 30° C. Cells were harvested and resuspended as above in phosphate buffer plus ethanol and irradiated at 70° C. in the presence of 0.5 ml toluene as hereinbefore described. A constitutive mutant, less affected then mutant C by catabolite repression was selected which gave an absorbance at 265 nm of 61.2. (Mutant strain C under identical conditions produced an absorbance of 15.6). This mutant is hereinafter referred to for convenience as mutant strain D.

The invention is illustrated by the following Example:

EXAMPLE

Production of cis-1,2-dihydroxy-3-trifluoromethylcyclohexa-3,5-diene by the process of the invention Mutant D was grown overnight at 30° C. with shaking in 200 ml of Bauschop and Elsdon's medium containing 1% w/v sodium pyruvate. The 200 ml culture was then used to inoculate 10 liters of a medium containing concentrated phosphoric acid (2.2 $g.l^{-1}$), $mgSO_4$ $7H_2O$ (0.8 $g.l^{-1}$), $K_2SO_4$ (0.45 $g.l^{-1}$), $(NH_4)_2SO_4$ (5 $g.l^{-1}$), $FeSO_4$ $7H_2O$ (0.04 $g.l^{-1}$), $CuSO_4$ $5H_2O$ (1 $mg.l^{-1}$), $MnSO_4 4H_2O$ (5 $mg.l^{-1}$), $CaCO_3$ (65 $mg.l^{-1}$) adjusted to pH 6.8 with 4M sodium hydroxide. This was stirred at 500 rpm, maintained at 28° C. and ¼ vvm. air was added. Glucose was added from a 40% w/v concentrated solution at a rate of 1 $g.l^{-1}.h^{-1}$ and the pH was maintained at 6.8 by automatic titration with 4M NaOH. All solutions were sterilised by autoclaving at 121° C. for 1 hour prior to use.

After 16 hours the cell density in the fermenter was 5 $g.l^{-1}$.

To 5 liters of the culture 20 ml absolute ethanol was added. The pH was increased to 7.3 and temperature and stirring maintained at 28° C. and 500 rpm respectively. Air was added at ¼ vvm. 1,1,1-trifluorotoluene was added to the culture as a liquid at a rate of 12 $ml.h^{-1}$. Further aliquots of ethanol of 10 ml and 7.5 ml were added after 2.5 h and 3.5 h. After 7 h the contents of the fermenter were centrifuged (10,000 g for 30 mins) and the supernatant retained. This was concentrated from 5 l to 0.5 l under vacuum by rotary evaporation at 60° C., and then continuously extracted with 2 l of methylene chloride for 24 h. The methylene chloride solution was concentrated under vacuum to 200 ml and sufficient pentane was added to cause crystallisation. The crystals (34 g) were collected by filtration and dried under vacuum.

NB: Cis-1,2-dihydroxy-3-trifluoromethyl-cyclohexa-3,5-diene has the structural formula

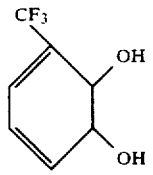

The product had the following characteristics:

| | |
|---|---|
| 1. | Melting point<br>90–91.5° C. (uncorrected) |
| 2. | Elements for CH analysis for $C_7F_3O_2$ |
| | Expected / Found<br>C 46.67 / 46.9<br>H 3.92 / 4.0 |
| 3. | Ifra-red (main bands)<br>γmax (liq. film) 3340(—OH), 1662, 1600 (c = c), 1310, 1275, 1175, 1110, 1000 and 800 $cm^{-1}$. |
| 4. | N.m.r. |
| 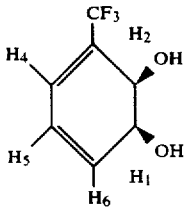 | δH($CDCl_3$, ppm from TMS) 4.0 and 4.25 (2H, broad singlets, $H_1$ and $H_2$), 6.0 (2H, multiplet, $H_5$ and $H_6$), 5.05 and 5.25 (2H, broad singlets —OH's) and 6.6 (1H, multiplet, $H_4$) |
| 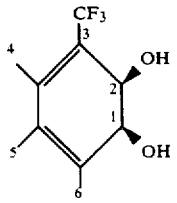 | δC<br>($CDCl_3$, chemical shift from TMS) 62.6 (C2), 69.7 (C1) 120.3 (C5), 124.5 (C3 $J_{C-F}$ 29$H_2$), 127.3 (C4, $S_{C-F}$ 6.5 $H_2$), 127.3 (—$CF_3$, $J_{C-F}$ 271 $H_2$) and 138.5(C6). |
| 5. | Mass spectroscopy<br>mol ion at m/2 180, fragments at 162, 151, 143 and 134. |

We claim:

1. Compounds having the general formula:

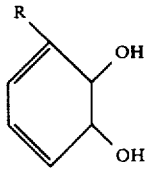

wherein R is selected from the group consisting of a —C trihalide, [an —O alkyl] and an —O phenyl group.

2. A compound according to claim 1 wherein R is $CF_3$.

3. A process for the production of a cyclic dihydroxy compound having the general formula:

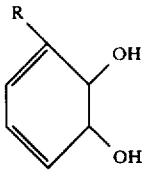

wherein R is selected from the group consisting of a —C trihalide, [an —O alkyl] and an —O phenyl group, which comprises supplying a corresponding substituted aromatic compound, having the general formula:

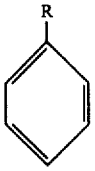

and an energy source to a strain which is a first mutant strain or a constitutive mutant strain of Pseudomonas putida (both as hereinbefore defined) in a medium which supports little or no growth of cells of the strain.

4. A process according to claim 3 wherein the substituted aromatic compound and the product have formulae in which R is —$CF_3$.

5. A process according to claim 3 wherein the source of energy is selected from the group consisting of ethanol and acetic acid.

6. A process according to claim 3 wherein the first mutant strain is derived from a Pseudomonas putida strain selected from the group consisting of NCIB 11680 or NCIB 11767.

7. A process according to claim 3 wherein the concentration of cells in the medium is in the range 1 to 30 grams dry weight per liter.

8. A process according to claim 3 wherein the temperature is in the range 20° C. to 40° C.

9. A process according to claim 3 wherein the pH of the medium is in the range 6.5 and 8.5.

10. A process according to claim 3 wherein oxygen or an oxygen-containing gas is supplied to the medium to maintain the oxygen tension therein at greater than 1% of saturation.

* * * * *